(12) United States Patent
Lin et al.

(10) Patent No.: US 12,090,663 B2
(45) Date of Patent: Sep. 17, 2024

(54) ROBOT ARM CONTROL METHOD AND SKIN SURFACE TREATMENT APPARATUS

(71) Applicant: Chun Man Anthony Lin, Hong Kong (CN)

(72) Inventors: Chun Man Anthony Lin, Hong Kong (CN); Chi Kit Curie Lee, Hong Kong (CN); Domingo Gomez Dominguez, Huelva (ES)

(73) Assignee: Lin Chun Man Anthony, Hong Kong (CN)

( * ) Notice: Subject to any disclaimer, the term of this patent is extended or adjusted under 35 U.S.C. 154(b) by 0 days.

(21) Appl. No.: 17/628,564

(22) PCT Filed: Jul. 23, 2021

(86) PCT No.: PCT/CN2021/108045
§ 371 (c)(1),
(2) Date: Jan. 20, 2022

(87) PCT Pub. No.: WO2022/017485
PCT Pub. Date: Jan. 27, 2022

(65) Prior Publication Data
US 2023/0356394 A1 Nov. 9, 2023

(30) Foreign Application Priority Data

Jul. 23, 2020 (CN) .......................... 202010714728.6

(51) Int. Cl.
*B25J 9/16* (2006.01)
*B25J 11/00* (2006.01)
*B25J 13/08* (2006.01)
(52) U.S. Cl.
CPC ........... *B25J 9/1664* (2013.01); *B25J 9/1602* (2013.01); *B25J 9/1697* (2013.01); *B25J 11/008* (2013.01); *B25J 13/087* (2013.01)

(58) Field of Classification Search
CPC ...... B25J 9/1664; B25J 9/1602; B25J 9/1697; B25J 11/008; B25J 13/087
See application file for complete search history.

(56) References Cited

U.S. PATENT DOCUMENTS

2015/0009214 A1* 1/2015 Lee .......................... G06T 17/10
345/420
2018/0374186 A1* 12/2018 McMurrough ........... G06T 7/70
(Continued)

FOREIGN PATENT DOCUMENTS

CN 106971147 A * 7/2017
CN 110110672 A * 8/2019

*Primary Examiner* — Behrang Badii
*Assistant Examiner* — Jay Khandpur
(74) *Attorney, Agent, or Firm* — George G. Wang; Bei & Ocean

(57) ABSTRACT

Disclosed are a robot arm control method, a skin surface treatment apparatus, and a computer-readable memory medium, which relate to the field of mechanical control. the robot arm control method includes steps of: demarcating a to-be-treated surface of an object treated by a robot arm into at least two areas of interest; obtaining, by a three-dimensional scanning device, a three-dimensional point cloud corresponding to each area of interest; optimizing respective three-dimensional point clouds; merging the respective three-dimensional point clouds to obtain an executive point cloud; creating a motion path for the robot arm based on the executive point cloud; and performing, by the robot arm, a treatment to the surface of the object based on the motion path. Compared with conventional technologies, the disclosure has a better cost-effectiveness, an enhanced treatment efficiency, and an improved apparatus safety.

9 Claims, 7 Drawing Sheets

(56) References Cited

U.S. PATENT DOCUMENTS

| | | | | |
|---|---|---|---|---|
| 2020/0118281 A1* | 4/2020 | Kwon | .................. | G06V 20/647 |
| 2021/0040757 A1* | 2/2021 | Abadi | ........................ | B25J 5/00 |
| 2021/0339399 A1* | 11/2021 | Schluntz | .............. | G05D 1/0088 |

* cited by examiner

ROBOT ARM CONTROL METHOD AND SKIN SURFACE TREATMENT APPARATUS

FIELD

Embodiments of the present disclosure relate to mechanical control, and more particularly relate to a robot arm control method for skin surface treatment and a skin surface treatment apparatus.

BACKGROUND

Skin beautification as a non-invasive cosmetic procedure includes non-therapeutic adornment methods applied locally to visible body parts such as skin and hair, which can improve undesired skin conditions, enhance skin health, and slow skin aging.

Skin beautification treatments can improve the following conditions, but not limited thereto: stains, acnes, large pores, irritations from hair removal, wrinkles, and skin pigmentations, and can restore normal metabolism of the skin.

Skin beautification improves the skin comprehensively from four aspects: skin color, skin type, skin age, and skin health, and acts deeply into different layers of the skin to thoroughly resolve skin problems in terms of symptom, metabolism, root cause, and long-term management.

A skin treatment operation usually involves a plurality of instruments such as a cosmetic laser, an IPL (Intense Pulsed Light) machine, a RF (Radio Frequency) instrument, an ultrasonic skin tightening machine, a hair remover, and a high-pressure water injection nozzle. These instruments are generally manipulated by trained practitioners, incurring high labor costs. Besides, excessive and various human interventions cannot ensure or provide a stable, whole-process controllable service quality, which are also prone to medical accidents due to inexperienced or careless operations.

During a process of human body surface treatment, the robot arm grasps such cosmetic instruments or tools to provide stable, non-therapeutic skin beautification services in conjunction with various types of peripheral sensors. Thanks to its motion characteristics, the robot arm may move along the geometric profile of a human body surface. Therefore, it is needed to design a motion trajectory for the robot arm so as to ensure that the robot arm avoids a sensitive area of the human body surface or a special area forbidden to apply treatment (e.g., the area around the eyes or wounds) for the sake of safety.

To this end, conventional technologies attempt to leverage a three-dimensional scanning device to obtain three-dimensional (3D) point clouds of a human body surface and create a motion path for the robot arm based on the three-dimensional point clouds.

However, when treating an entire skin surface part, the generated three-dimensional point clouds have a huge amount of data. Specifically, dependent on camera resolution and data acquisition amount, hundreds of thousands of data points may be created by only scanning a human face. Since the robot arm moves in a point-to-point trajectory, it is impractical for the robot arm to move based on so many data points; therefore, it is needed to optimize the three-dimensional point clouds.

Moreover, for a huge amount of three-dimensional point clouds, their input, storage, optimization and output pose stringent demands on properties of a controller. If the controller does not satisfy the demands, data overflow likely occurs.

SUMMARY

To solve all or part of the above and other technical problems, embodiments of the present disclosure provide a robot arm control method.

The robot arm control method comprises steps of:
- demarcating a to-be-treated surface of an object treated by a robot arm into at least two areas of interest;
- obtaining, by a three-dimensional scanning device, a three-dimensional point cloud corresponding to each area of interest;
- optimizing respective three-dimensional point clouds;
- merging the respective three-dimensional point clouds to obtain an executive point cloud;
- creating a motion path for the robot arm based on the executive point cloud;
- and performing, by the robot arm, a treatment to the surface of the object based on the motion path.

Embodiments of the present disclosure further provide a skin surface treatment apparatus, comprising:
- a three-dimensional scanning device, a robot arm, and a controller;
- wherein the controller is configured to partition a to-be-treated surface of an object treated by the robot arm into at least two areas of interest;
- the three-dimensional scanning device is configured to obtain a three-dimensional point cloud corresponding to each area of interest;
- the controller is configured to optimize respective three-dimensional point clouds, merge the respective three-dimensional point clouds to obtain an executive point cloud, and create a motion path for the robot arm based on the executive point cloud;
- and the robot arm is configured to perform a treatment to the surface of the object based on the motion path.

Embodiments of the present disclosure further provide a computer-readable memory medium which stores a computer program, wherein the computer program, when being executed, can implement the steps of the method.

Embodiments of the present disclosure further provide a skin surface treatment apparatus, comprising: a memory, a processor, and a communication component, wherein:
- the memory is configured to store a program;
- the processor is coupled to the memory and configured to execute the program stored in the memory so as to:
- partition a to-be-treated surface of an object treated by a robot arm into at least two areas of interest;
- obtain, by a three-dimensional scanning device, a three-dimensional point cloud corresponding to each area of interest;
- optimize respective three-dimensional point clouds;
- merge the respective three-dimensional point clouds to obtain an executive point cloud;
- create a motion path for the robot arm based on the executive point cloud;
- and performing, by the robot arm, a treatment to the surface of the object based on the motion path.

Compared with conventional technologies, embodiments of the present disclosure offer the following advantages:

1. treatment safety of the robot arm is ensured by preliminarily scanning the surface of a to-be-treated object so as to identify and define an area forbidden to treat by the robot arm.

2. Data are segmented by demarcating the surface of the treated object into a plurality of areas of interest;
3. The amount of data of a single three-dimensional point cloud is reduced by canceling useless three-dimensional point cloud data through filtering and optimization;
4. An executive point cloud which has a small amount of data and may be precisely executed is obtained by merging a plurality of three-dimensional point clouds.

Therefore, compared with conventional technologies, the embodiments of the present disclosure are less demanding on properties of a controller, may reduce manufacturing costs of a skin surface treatment apparatus, and enhances treatment efficiency of the skin surface treatment apparatus.

BRIEF DESCRIPTION OF THE DRAWINGS

To illustrate the technical solutions in embodiments of the present disclosure or in conventional technologies, the drawings used in describing the embodiments or the conventional technologies will be briefly introduced below. It is apparent that the drawings as described only relate to some embodiments of the present disclosure. To those skilled in the art, other drawings may be derived based on these drawings without exercise of inventive work; the technical features, connection relationships, and even method steps not mentioned in other drawings may also be derived based on these drawings.

Figure 1:
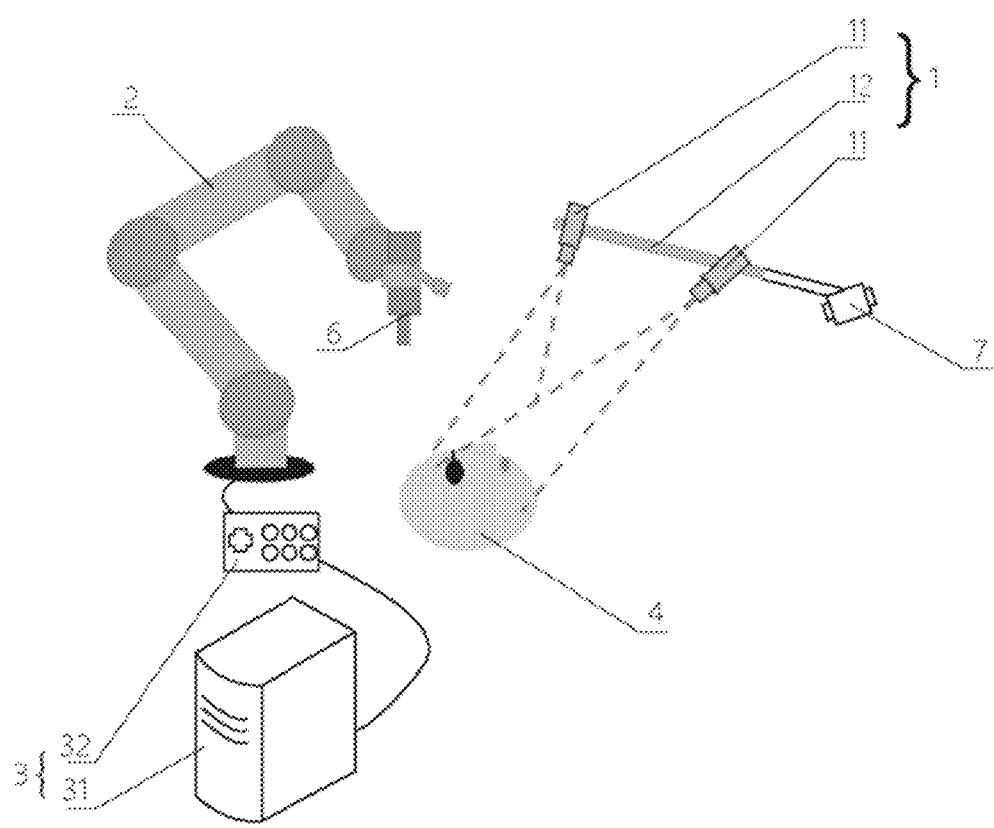
FIG. 1 is a schematic diagram of arranging two depth cameras on a same structural element according to an embodiment of the present disclosure.

REFERENCE NUMERALS 1. 3D scanning device; 11. depth camera; 12. structural element; 2. robot arm; 3. controller; 31. master computer; 32. slave control module; 4. surface of treated object;
51. memory; 52. processor; 53. communication component; 54. display; 55. power supply component; 56. audio component; 6. surface treatment instrument; 7. sensor.

DETAILED DESCRIPTION

Hereinafter, the present disclosure will be described in further detail with reference to the accompanying drawings:

First Embodiment

As discussed in the Background section, conventional technologies fail to provide a robot arm control method with good cost-effectiveness and high performance.

Figure 2:
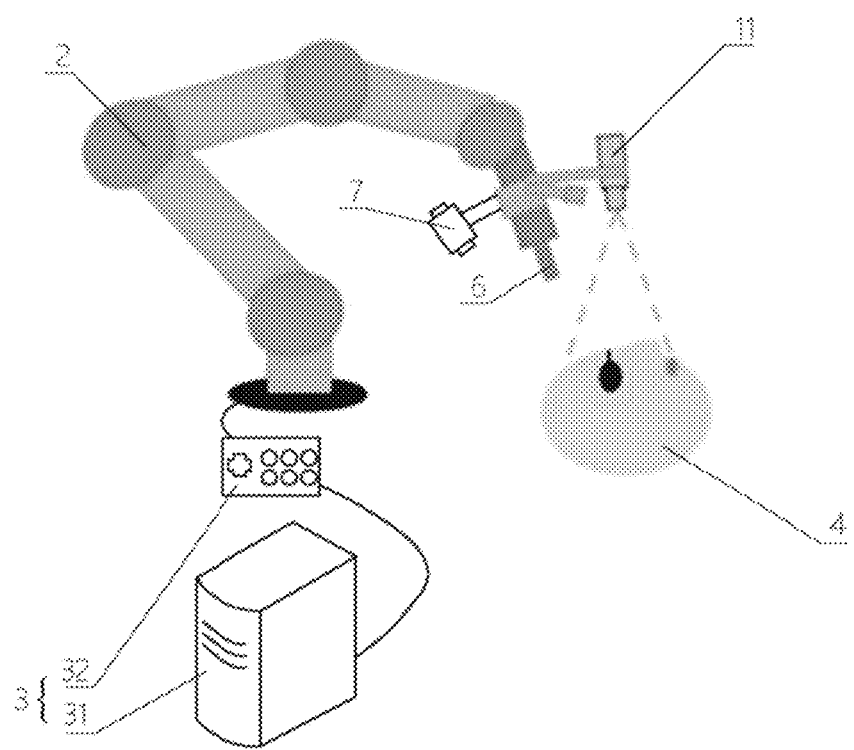
FIG. 2 is a schematic diagram of arranging one depth camera on a robot arm according to an embodiment of the present disclosure.

In view of the above, a first embodiment of the present disclosure provides a skin surface treatment apparatus, as shown in FIG. 1 or FIG. 2, wherein the skin surface treatment apparatus comprises:

a three-dimensional scanning device 1, a robot arm, 2 and a controller 3;

wherein the controller 3 is configured to partition a to-be-treated surface of an object treated by the robot arm 2 into at least two areas of interest;

the three-dimensional scanning device 1 refers to a device configured to obtain a three-dimensional point cloud of a stereoscopic surface of an object. In an embodiment of the present disclosure, the three-dimensional scanning device 1 is configured to obtain a three-dimensional point cloud corresponding to each area of interest;

the controller 3 is configured to optimize respective three-dimensional point clouds, merge the respective three-dimensional point clouds to obtain an executive point cloud, and create a motion path for the robot arm 2 based on the executive point cloud; and the robot arm 2 is configured to perform a corresponding treatment to the surface 4 of the object based on the motion path.

In an embodiment of the present disclosure, surface treatment instruments 6 for various purposes may be installed on the robot arm 2, for example, a cosmetic laser, an IPL machine, a RF instrument, an ultrasonic skin tightening machine, a hair remover, and a high-pressure water injection nozzle, etc. Such surface treatment instruments 6 may be electrically connected with the controller 3 so as to act in cooperation with the motion path of the robot arm 2.

It is understood that the controller 3 refers to a controller in a broad sense, which may be partially disposed discretely external to the robot arm 2 or may be entirely integrated in the robot arm 2. Typically, as illustrated in FIG. 1 or FIG. 2, the controller 3 may comprise a slave control module 32 installed on the robot arm 2 and a master computer 31 (e.g., computer workstation, or other mobile or immobile terminal) connected to the slave control module 32. If the controller 3 comprises both of the slave control module 32 and the master computer 31, the master computer 31 is configurable to analyze and process the data captured and collected by the three-dimensional scanning device 1 to obtain action data of the robot arm. Then, the master computer 31 outputs the action data into the slave control module 32 so as to implement operation logic of the robot arm 2 via the slave control module 32.

Additionally, the slave control module 32 may be a controller inherent in the robot arm 2, which not only provides a control interface for the robot arm 2, but is also configurable to supply power to the robot arm 2.

Optionally, the three-dimensional scanning device 1 may include two depth cameras 11 statically installed on a same structural element 12. Referring to FIG. 1, in this optional example, two depth cameras 11 may be provided and installed on the structural element 12. The structural element 12 may be a support frame or a typical fixture. Position of the structural element 12 may be calibrated via a scale and is adaptable for different sizes of treated objects. After the depth cameras 11 are fixed, coordinates of the depth cameras 11 may be preset in the controller 3 so as to maintain calibrated.

During scanning the surface of an object, each depth camera 11 generates a three-dimensional point cloud. On this basis, a side surface of the to-be-treated object may be plotted via each depth camera 11. For example, with a human face as a to-be-treated object, the three-dimensional point clouds of the left and right sides of the face may be simultaneously plotted using the depth cameras 11 disposed to the left and right of the human face. Further optionally, when the treated object is a human face, there may be 6 to 8 areas of interest; correspondingly, the number of depth cameras 11 may be correspondingly adjusted as needed.

In this way, the controller 3 may optimize and merge these three-dimensional point clouds to thereby obtain an executive point cloud and further create a motion path for the robot arm 2, and then drive the robot arm 2 to move along the motion path.

Of course, when more depth cameras 11 are adopted, each of these depth cameras 11 corresponds to a respective area of interest, thereby significantly enhancing scanning efficiency.

Optionally, the three-dimensional scanning device 1 may include one or more depth cameras 11 installed on the robot arm 2.

In an optional example illustrated in FIG. 2, a single depth camera 11 may be provided, which is installed on the robot arm 2.

In the controller 3, the exact position of the robot arm 2 may be known at any time based on the motion path of the robot arm 2, and thus the exact position of the depth camera 11 may be likewise obtained. Therefore, under control by the controller 3, during the course of the robot arm's moving across the to-be-treated object along a preset trajectory, a plurality of three-dimensional point clouds may be obtained by the single depth camera 11. For each three-dimensional point cloud data, the controller 3 may calibrate the coordinate data of the single depth camera 11 when capturing the three-dimensional point cloud, wherein the coordinate data are available for subsequent processing.

In this way, the controller 3 may likewise optimize and merge these three-dimensional point clouds to thereby obtain an executive point cloud and further create a motion path for the robot arm 2, and then drive the robot arm 2 to move along the motion path.

When the robot arm 2 is only installed with a single depth camera 11, a need of configuring a plurality of depth cameras 11 is eliminated, which may significantly reduce costs.

Figure 3:
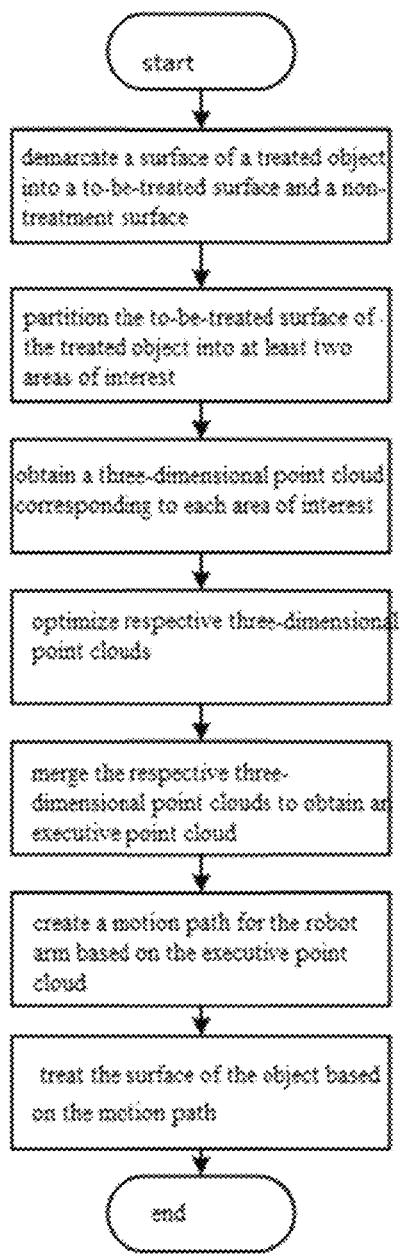
FIG. 3 is a simplified flow diagram of a robot arm control method according to an embodiment of the present disclosure.

In another aspect, embodiments of the present disclosure further provide a robot arm control method, as illustrated in FIG. 3, which comprises steps of:
  demarcating a to-be-treated surface of an object treated by a robot arm 2 into at least two areas of interest;
  obtaining, by a three-dimensional scanning device 1, a three-dimensional point cloud corresponding to each area of interest;
  optimizing respective three-dimensional point clouds;
  merging the respective three-dimensional point clouds to obtain an executive point cloud;
  creating a motion path for the robot arm 2 based on the executive point cloud;
  performing, by the robot arm 2, a treatment to the surface of the object based on the motion path.

Optionally, the controller 3 may analyze the surface 4 of the treated object through preliminary scanning so as to identify and define an area forbidden for treatment by the robot arm 2. In other words, before the step of demarcating a to-be-treated surface of the object treated by the robot arm into at least two areas of interest, the method may further comprise a step of: pre-scanning the surface 4 of the treated object so as to demarcate the surface 4 of the treated object into a to-be-treated surface and a non-treatment surface. The to-be-treated surface literally refers to a surface the needs to be treated, while the non-treatment surface literally refers to a surface that does not need treatment. The non-treatment surface may refer to a wound on the skin, a special organ such as eyes, ears, nipples, navel, etc., or a skin area not desired to treat.

The pre-scanning may be implemented in a fast scan mode, which cancels the non-treatment surface, and thus may reduce the time for subsequent refined scan and treatment of the areas of interest, thereby significantly enhancing operation efficiency of the robot arm. Preferably, the to-be-treated surface and the non-treatment surface may be automatically recognized using an AI image recognition technology. Of course, after AI image recognition, the recognized area may be manually reviewed so as to ensure accuracy.

After the depth camera obtains three-dimensional point clouds from the areas of interest, it is likely that the obtained three-dimensional point clouds cannot be directly used due to the huge amount of data. Therefore, the respective three-dimensional point clouds may be optimized in various manners so as to reduce computational complexity.

Figure 6:
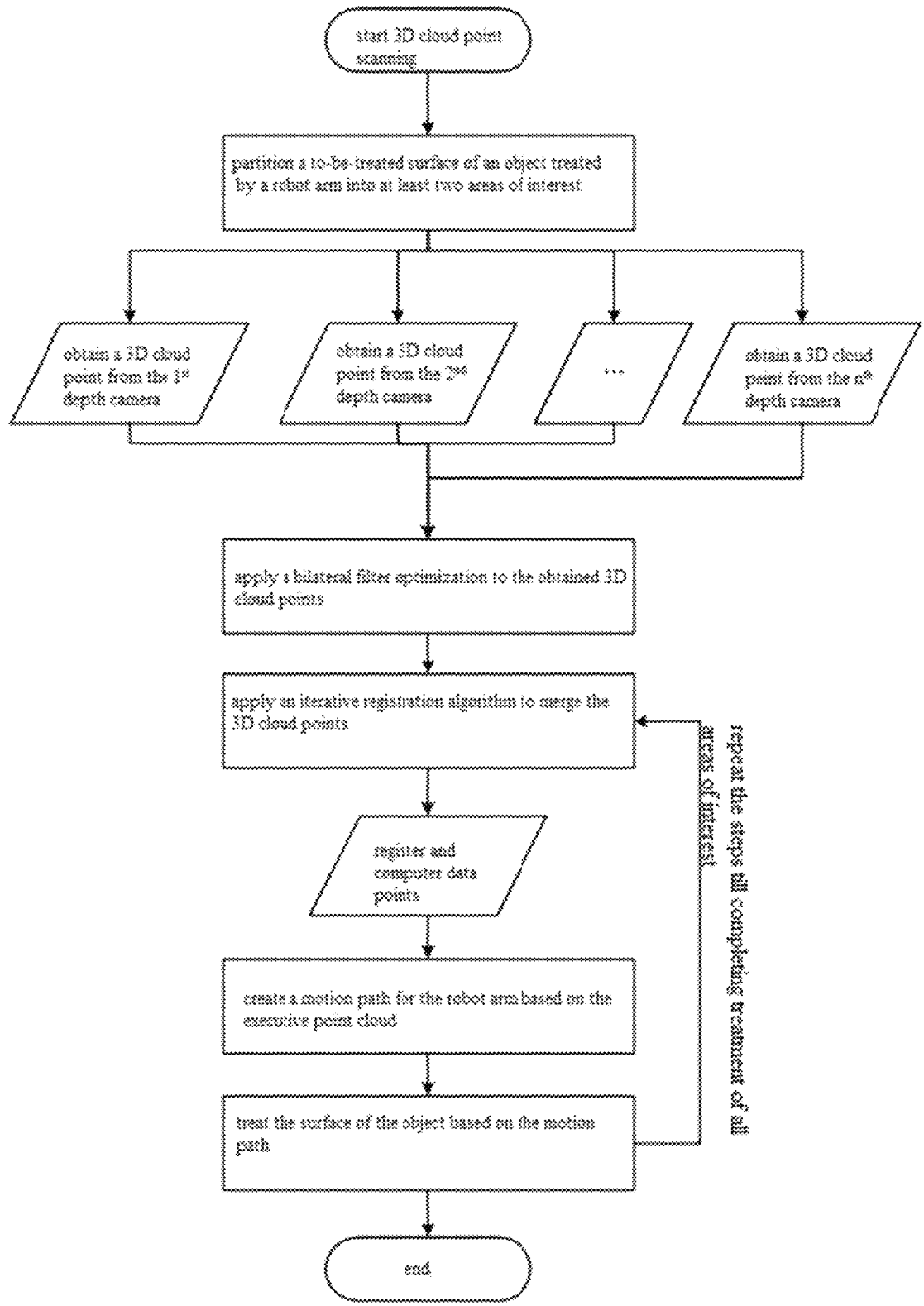
FIG. 6 is a flow diagram of a robot arm control method during a process of treating a to-be-treated surface according to an embodiment of the present disclosure.

In an optional embodiment, as shown in FIG. 3 and FIG. 6, the step of optimizing the respective three-dimensional point clouds may comprise:
  performing filter processing to the three-dimensional point clouds using a bilateral filter so as to reduce their noises.

The bilateral filter is used for image denoising. There are a plurality of methods for image denoising, e.g., median filter, Gauss filter, and Wiener filter, etc. However, such denoising methods are prone to blurring edge details of an image, without a notable protection effect for high-frequency details. In contrast, the bilateral filter may provide a good edge protection, i.e., protecting edge properties of the image while denoising. The inventors of the present application discover that, for the technical solution of creating a motion path for the robot arm 2, definition degree of the edge properties of the image is critical to render an optimal motion path.

In an embodiment of the present disclosure, a kernel of the bilateral filter adopted may be mathematically expressed as:

$$I^{filtered}(x) = \frac{1}{W_p} \sum_{x_i \in \Omega} I(x_i) f_r(\|I(x_i) - I(x)\|) g_s(\|x_i - x\|)$$

$$W_p = \sum_{x_i \in \Omega} f_r(\|I(x_i) - I(x)\|) g_s(\|x_i - x\|)$$

where $\Omega$ denotes a window with x as the center, wherein x denotes a range kernel for smoothing an intensity difference, while $g_s$ denotes a spatial kernel for smoothing a coordinate difference.

Figure 4:
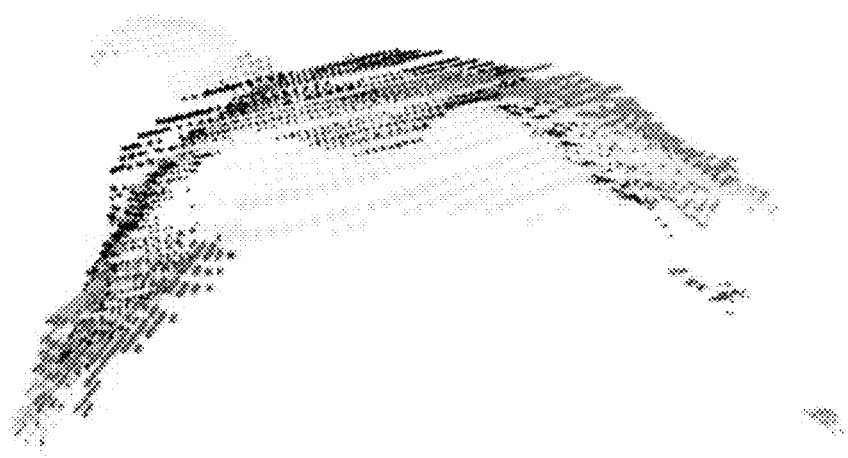
FIG. 4 is a schematic diagram of a three-dimensional point cloud before optimization and filtering according to an embodiment of the present disclosure.
Figure 5:
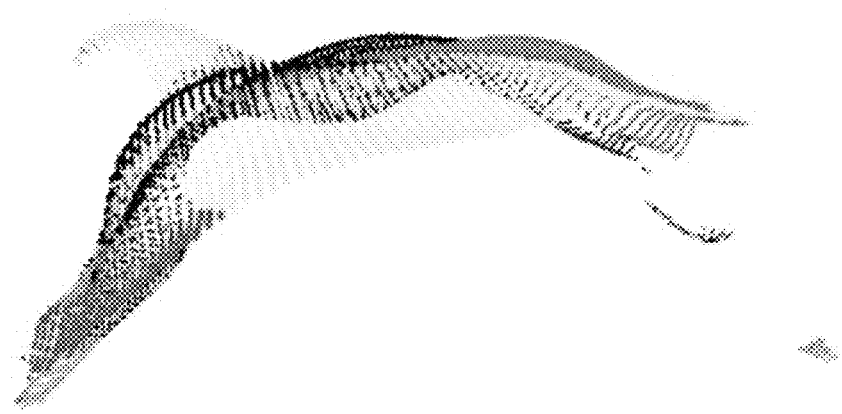
FIG. 5 is a schematic diagram of a three-dimensional cloud point after being optimized and filtered according to an embodiment of the present disclosure.

FIG. 4 and FIG. 5 show three-dimensional point cloud changes before and after adopting the bilateral filter, from which it is seen that a sharp and definite three-dimensional point cloud with less noise may be obtained after filtering by the bilateral filter.

Optionally, the step of merging the respective three-dimensional point clouds to obtain an executive point cloud may comprise:

merging a first three-dimensional point cloud and a second three-dimensional point cloud to a new three-dimensional point cloud by iteratively registering the closest points between the first three-dimensional point cloud and the second three-dimensional point cloud, and then performing iterative registration between the merged new three-dimensional point cloud and a next three-dimensional point cloud, and so forth till all three-dimensional point clouds are merged into the executive point cloud.

Registration refers to a process of finding, given two three-dimensional data point-sets from different coordinate systems, a transformation relationship between two point-set spaces such that the two point-sets can be integrated into a same coordinate system.

The iterative registration algorithm employed in the embodiments of the present disclosure may also be referred to as an Iterative Closest Point (ICP) algorithm, which is a three-dimensional point cloud matching algorithm. This algorithm allows merging of different three-dimensional point clouds obtained from different depth cameras (or a same depth camera at different positions) into a single three-dimensional point cloud, wherein the three-dimensional point clouds are translated and rotated to match without deformation, till reaching the minimum error.

The amount of data of the executive point cloud obtained through this algorithm is far smaller than that of the initial three-dimensional point clouds obtained by the three-dimensional scanning device 1, thereby being easily processed and executed by the controller 3.

Specifically, the executive point cloud has a single coordinate origin representing three-dimensional (3D) information. This coordinate origin may be selected identical to that of any depth camera 11. Since the position of the coordinate origin is known and associated with the coordinates of the robot arm, compensation may be applied to the executive point cloud to create a motion path for the robot arm 2.

The motion path based on the executive point needn't consider computation of the positional relationships due to different coordinate origins between the three-dimensional cloud points obtained by respective depth cameras 11, thereby significantly reducing computational complexity.

Therefore, compared with conventional technologies, the technical solution of the present disclosure can reduce computational complexity and enhance system performance.

It is further noted that in an embodiment of the present disclosure, the executive point cloud resulting from merging the three-dimensional cloud points in the merging step may be a product of merging the respective three-dimensional point clouds of one or two areas of interest, or a final point cloud resulting from merging the three-dimensional point clouds of all areas of interest. Dependent on the amount of data, the execution may be performed by the robot arm 2 at one time after all of the three-dimensional point clouds are merged; or, as illustrated in FIG. 6, the three-dimensional cloud points are executed by the robot arm 2 while being merged. Therefore, optionally, the motion path may be formed by connecting one covered area of interest to the next area of interest, thereby facilitating the robot arm 2 to perform a treatment operation.

In conventional technologies, the motion path of the robot arm 2 created by directly using the three-dimensional point clouds obtained by the three-dimensional scanning device 1 has a too huge amount of data if such motion path is not subjected to good data processing, which is highly demanding on the operating system of the robot arm 2.

Compared with conventional technologies, embodiments of the present disclosure offer the following advantages:

1. Treatment safety of the robot arm is ensured by preliminarily pre-scanning the surface 4 of a treated object so as to identify and define an area forbidden for treatment by the robot arm.
2. The amount of data is segmented by demarcating the surface 4 of the treated object into a plurality of areas of interest;
3. The amount of data of a single three-dimensional point cloud is reduced by cancelling useless three-dimensional point cloud data through filtering and optimization;
4. An executive point cloud which has a small amount of data and may be precisely executed is obtained by merging a plurality of three-dimensional point clouds.

Therefore, compared with conventional technologies, the embodiments of the present disclosure are less demanding on properties of the controller 3, which may reduce manufacturing costs of a skin surface treatment apparatus, and enhance treatment efficiency of the skin surface treatment apparatus. With the robot arm in replacement of conventional manual treatment, quality stability and treatment safety of skin surface treatment operations are enhanced.

Second Embodiment

The second embodiment is further improvement to the first embodiment. The main improvement lies in that in the second embodiment of the present application, the step of performing, by the robot arm 2, a treatment to the surface 4 of the treated object based on the motion path in the robot arm control method, as illustrated in FIGS. 1 and 2, further comprises:

obtaining, by a sensor 7, status data of the surface of the treated object;

and adjusting a treatment operation of the robot arm 2 based on the status data.

Correspondingly, the skin surface treatment apparatus comprises: a sensor 7 configured to obtain status data of the surface of the treated object;

and a controller 3 configured to adjust a treatment operation of the robot arm 2 based on the status data.

Optionally, the status data may include temperature or humidity.

In the present disclosure, the sensor 7 may refer to a device for detecting a status of a human body skin. The sensor 7 comes in various types: for example, a temperature sensor 7 configurable to measure temperature of a skin surface; a humidity sensor 7 configurable to measure humidity of the skin; a camera configurable to detect texture of the skin; and a spectroscopy sensor 7 configurable to measure spectrum or laser energy irradiated to the skin. The sensor 7 may be positioned consistent with the depth camera 11. In other words, when the depth camera 11 is arranged on a structural element 12, the sensor 7 may also be arranged on the structural element 12; while when the depth camera 11 is arranged on the robot arm 2, the sensor 7 may also be arranged on the robot arm 2.

Of course, when a plurality of depth cameras 11 are arranged on the structural element 12, the sensor 7 may be arranged on the robot arm 2 so as to move with the robot arm to more accurately and promptly give a status data feedback regarding the current operating area. Moreover, arranging the sensor 7 on the robot arm 2 may also prevent the sensor 7 from being blocked during motion of the robot arm 2, thereby enhancing data accuracy.

Now, treatment operations regarding how to adjust the robot arm 2 based on the status data will be explained with some typical sensors 7 as examples.

When the sensor 7 refers to a temperature sensor 7, the temperature sensor 7 may detect a temperature of a working area of a treatment instrument (e.g., the laser) on the robot arm 2 and transmit the temperature to the controller 3.

Since skin temperature rises upon irradiation by the laser, when the controller 3 detects that the temperature rise reaches or exceeds a threshold, it may control the laser to lower its output power or control the laser to turn off, or even accelerate movement of the robot arm 2 along the motion path, thereby shortening the dwell time of the laser on the skin surface where the temperature rise exceeds the threshold.

When the sensor 7 refers to a humidity sensor 7, the humidity sensor 7 may detect a humidity of the working area of a treatment instrument on the robot arm 2, and transmit the temperature to the controller 3.

When the skin humidity drops, injury might occur. When the controller 3 detects that humidity drop reaches or exceeds a threshold, it may control the laser to lower the output power, or control a high-pressure nozzle to spray water, or control an atomizer to atomize for supplementing skin moisture, etc.

When the sensor 7 refers to a spectroscopy sensor 7, the spectroscopy sensor 7 may detect a laser energy received by the working area of a treatment instrument on the robot arm 2, and transmit the laser energy to the controller 3.

Injury is prone to occur when the skin receives a too intensive laser energy in a short time. When the controller 3 detects that laser energy rise reaches or exceeds a threshold, it may control the laser to lower its output power or control the laser to turn off, or even accelerate movement of the robot arm 2 along the motion path, thereby shortening the dwell time of the laser on the skin surface where the accumulated laser energy exceeds the threshold.

Dependent on the therapeutic procedure and laser technology applied, the temperature information fed back by the sensor 7 may be used to stabilize safety margin of temperature, the humidity information may be used to optimize and enhance user experience, and the laser energy information may be used to accurately indicate output dosage of the laser energy.

Additionally, in an optional embodiment, the step of obtaining, by the sensor 7, the status data of the object surface may further comprise: when the status data exceeds a threshold, adjusting the motion path to temporarily avoid a part where the object surface exceeds the threshold.

Third Embodiment

A third embodiment of the present disclosure provides a computer-readable memory medium which stores a computer program, wherein the computer program, when being executed, can implement the steps of the method according to the first or second embodiment.

The computer program enables automatic performance of the above steps with improved efficiency.

Figure 7:
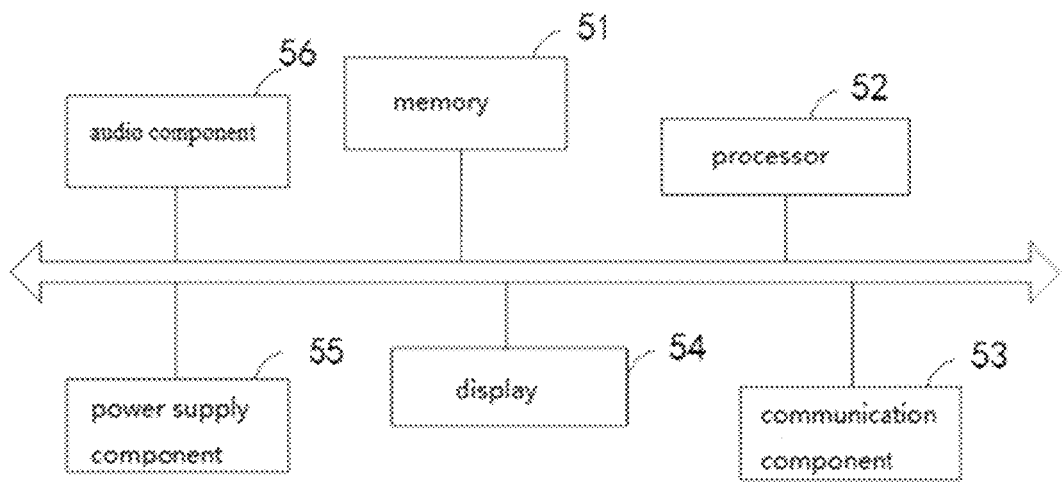
FIG. 7 is a system block diagram of a skin surface treatment apparatus according to an embodiment of the present disclosure.

Therefore, embodiments of the present disclosure further provide a skin surface treatment apparatus, as illustrated in FIG. 7, comprising: a memory 51, a processor 52, and a communication component 53, wherein:

the memory 51 is configured to store a program;

the processor 52 is coupled to the memory 51 and configured to execute the program stored in the memory 51 so as to:

partition a surface 4 of an object treated by a robot arm 2 into at least two areas of interest;

obtain, by a three-dimensional scanning device 1, a three-dimensional point cloud corresponding to each area of interest;

optimize respective three-dimensional point clouds;

merge the respective three-dimensional point clouds to obtain an executive point cloud;

create a motion path for the robot arm 2 based on the executive point cloud;

perform, by the robot arm 2, a treatment to the surface of the object based on the motion path.

Furthermore, the skin surface treatment apparatus may further comprise: a communication component 53, a display 54, a power supply component 55, and an audio component 56. The present disclosure only schematically lists some components, which does not mean that the computing device only includes these elements.

Finally, it is noted that those of normal skill in the art may understand that many technical details provided in the various embodiments above are only for readers to understand better. However, the technical solutions as claimed in the claims of the present application may be still implemented substantially even without these technical details or various changes and modifications of the embodiments above. Therefore, in actual applications, various alterations to the embodiments may be made in forms and details without departing from the spirit and scope of the present disclosure.

We claim:

1. A robot arm control method, comprising steps of:

demarcating a to-be-treated surface of an object treated by a robot arm into at least two areas of interest;

obtaining, by a three-dimensional scanning device, a three-dimensional point cloud corresponding to each area of interest;

optimizing respective three-dimensional point clouds;

merging the respective three-dimensional point clouds to obtain an executive point cloud;

creating a motion path for the robot arm based on the executive point cloud; and performing, by the robot arm, a treatment to the surface of the object based on the motion path, wherein the treated object is a human face, and there are 6 or 8 areas of interest;

and the motion path connects each covered area of interest to a next area of interest.

2. The robot arm control method according to claim 1, wherein the step of optimizing respective three-dimensional point clouds comprises:

using a bilateral filter to filter and process the three-dimensional cloud points so as to reduce their noises.

3. The robot arm control method according to claim 1, wherein the step of merging the respective three-dimensional point clouds to obtain an executive point cloud comprises:

merging a first three-dimensional point cloud and a second three-dimensional point cloud to a new three-dimensional point cloud by iteratively registering the closest points between the first three-dimensional point cloud and the second three-dimensional point cloud, and then performing iterative registration between the merged new three-dimensional point cloud and a next three-dimensional point cloud, and so forth till all three-dimensional point clouds are merged into the executive point cloud.

4. The robot arm control method according to claim 1, wherein the step of performing, by the robot arm, a treatment to the surface of the object based on the motion path comprises:
   obtaining status data of the surface of the object via a sensor; and
   adjusting a treatment operation of the robot arm based on the status data;
   wherein the step of obtaining status data of the surface of the object via a sensor comprises: when the status data exceeds a threshold, adjusting the motion path to temporarily avoid a part of the surface of the object where the status data exceeds the threshold.

5. The robot arm control method according to claim 1, wherein before the step of demarcating a to-be-treated surface of the object treated by the robot arm into at least two areas of interest, the method further comprises a step of:
   pre-scanning the surface of the treated object so as to demarcate the surface of the treated object into a to-be-treated surface and a non-treatment surface.

6. A skin surface treatment apparatus, comprising: a three-dimensional scanning device, a robot arm, and a controller;
   wherein the controller is configured to partition a to-be-treated surface of an object treated by the robot arm into at least two areas of interest;
   the three-dimensional scanning device is configured to obtain a three-dimensional point cloud corresponding to each area of interest;
   the controller is configured to optimize respective three-dimensional point clouds, merge the respective three-dimensional point clouds to obtain an executive point cloud, and create a motion path for the robot arm based on the executive point cloud; and
   the robot arm is configured to perform a treatment to the surface of the object based on the motion path,
   wherein the treated object is a human face, and there are 6 or 8 areas of interest;
   and the motion path connects each covered area of interest to a next area of interest.

7. The skin surface treatment apparatus according to claim 6, wherein the three-dimensional scanning device includes two depth cameras installed on a same structural element; or, the three-dimensional scanning device includes a single depth camera installed on the robot arm.

8. The skin surface treatment apparatus according to claim 6, further comprising: a sensor configured to obtain status data of the surface of the object; wherein the controller adjusts a treatment operation of the robot arm based on the status data.

9. A skin surface treatment apparatus, comprising: a memory, a processor, and a communication component, wherein:
   the memory is configured to store a program;
   the processor is coupled to the memory and configured to execute the program stored in the memory so as to:
   partition a to-be-treated surface of an object treated by a robot arm into at least two areas of interest;
   obtain, by a three-dimensional scanning device, a three-dimensional point cloud corresponding to each area of interest;
   optimize respective three-dimensional point clouds;
   merge the respective three-dimensional point clouds to obtain an executive point cloud;
   create a motion path for the robot arm based on the executive point cloud; and
   performing, by the robot arm, a treatment to the surface of the object based on the motion path,
   wherein the treated object is a human face, and there are 6 or 8 areas of interest;
   and the motion path connects each covered area of interest to a next area of interest.

* * * * *